(12) United States Patent
Dalton et al.

(10) Patent No.: US 9,090,654 B2
(45) Date of Patent: *Jul. 28, 2015

(54) BOC AND FMOC SOLID PHASE PEPTIDE SYNTHESIS

(71) Applicant: Ipsen Manufacturing Ireland Limited, Dublin (IE)

(72) Inventors: Catherine Fiona Dalton, Donabate (IE); John Stuart Eynon, Bellingham, MA (US); Steven Allen Jackson, Newtonville, MA (US); Gary Alexander Siwruk, Franklin, MA (US)

(73) Assignee: IPSEN MANUFACTURING IRELAND LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 13/734,537

(22) Filed: Jan. 4, 2013

(65) Prior Publication Data

US 2013/0338337 A1 Dec. 19, 2013

Related U.S. Application Data

(63) Continuation of application No. 12/312,689, filed as application No. PCT/IE2007/000080 on Aug. 31, 2007, now Pat. No. 8,383,770.

(30) Foreign Application Priority Data

Nov. 21, 2006 (IE) .................................... 2006/0841

(51) Int. Cl.
*A61K 38/12* (2006.01)
*C07K 1/04* (2006.01)
*C07K 1/00* (2006.01)
*C07K 1/06* (2006.01)
*C07K 1/08* (2006.01)
*C07K 1/10* (2006.01)
*C07K 7/64* (2006.01)
*A61K 38/08* (2006.01)
*C07K 14/655* (2006.01)

(52) U.S. Cl.
CPC . *C07K 1/04* (2013.01); *A61K 38/08* (2013.01); *A61K 38/12* (2013.01); *C07K 1/003* (2013.01); *C07K 1/06* (2013.01); *C07K 1/061* (2013.01); *C07K 1/08* (2013.01); *C07K 1/10* (2013.01); *C07K 7/64* (2013.01); *C07K 14/6555* (2013.01)

(58) Field of Classification Search
CPC .............. C07K 1/00; C07K 7/00; C07K 1/08; C07K 1/10; C07K 1/061; C07K 1/062; C07K 1/063; C07K 1/065; C07K 1/067; C07K 17/14; A61K 38/00; A61K 38/08
See application file for complete search history.

(56) References Cited

U.S. PATENT DOCUMENTS 4,737,487 A  4/1988  Watts et al.

FOREIGN PATENT DOCUMENTS

EP  0 184 309      6/1986
WO  WO 2006/119388  11/2006

OTHER PUBLICATIONS

Isidro-Llobet et al., Chem. Rev. (2009) 109, 2455-2504.*
Andersson, et al. (2000) *Biopolymers (Peptide Science)* 55: 227-250.
Chersi, et al. (2006) *Analytical Biochemistry* 357: 194-199.
Gisin (1973) *Helv. Chim. Acta.*. 56(5): 142-143.

* cited by examiner

*Primary Examiner* — Karlheinz R Skowronek
*Assistant Examiner* — Catherine Mader
(74) *Attorney, Agent, or Firm* — Hunton & Williams LLP

(57) ABSTRACT

A solid phase method for synthesizing a peptide containing three or more amino acid residues utilizing both Boc and Fmoc protected amino acids and a chloromethylated polystyrene resin.

10 Claims, No Drawings

BOC AND FMOC SOLID PHASE PEPTIDE SYNTHESIS

CROSS-REFERENCE TO RELATED APPLICATIONS

This application is a continuation application of U.S. patent application Ser. No. 12/312,689, filed May 21, 2009, which is a national stage of International Application No. PCT/IE2007/000080, filed Aug. 31, 2007, which claims priority from IE 2006/0841, filed Nov. 21, 2006, the disclosures of each of which are herein incorporated by reference.

TECHNICAL FIELD

This invention relates to a method for preparing a peptide comprising three or more amino acid residues having an N-terminal amino acid, a next to last amino acid adjacent to the N-terminal amino acid and a C-terminal amino acid.

BACKGROUND ART

Solid phase peptide synthesis was introduced in 1963 with the intent to overcome many of the intermediate purification problems associated with solution peptide synthesis. Stewart, et al., Solid Phase Peptide Synthesis (Pierce Chemical Co., 2d ed., 1984). During solid phase synthesis, amino acids are assembled (i.e., coupled) into a peptide of any desired sequence while one end of the chain (i.e., the C-terminus) is anchored to an insoluble support. Once the desired sequence has been linked together on the support, the peptide is then deblocked (i.e., cleaved) from the support. The two standard protecting groups for α-amino functions of the coupled amino acids are Boc, which is removed by treatment with a strong acid, and Fmoc, which is removed with a base. The present invention relates to a convenient method of manufacturing peptides using a combination of both of these α-amino protecting groups in a single synthesis on inexpensive chloromethylated polystyrene resin.

In designing a synthesis of a peptide by the solid phase method using either of the above mentioned α-amino protection schemes, it is important that any reactive "side groups" of the constituent amino acids be protected from unwanted chemical reactions throughout the chain assembly. It is also desirable that the chemical groups chosen to protect the various side groups be resistant to removal by the reagents used to remove the α-amino protecting groups. Thirdly, it is important that the linkage of the growing peptide chain to the resin particle be stable to the reagents used to remove either type of α-amino protecting group during chain assembly. In the case of the Fmoc α-amino protection scheme, the side group protection functions should be resistant to the basic reagents used to remove the Fmoc. In practice, these side chain protecting groups are generally removed by mildly acidic reagents after the peptide chain has been assembled. When using the Boc α-amino protection scheme, the side chain protecting groups must be resistant to removal by the mild acid reagent used to deprotect the Boc group at every cycle. In practice, these side chain protecting groups for the Boc α-amino protection scheme are generally removed by anhydrous HF after the peptide chain has been assembled. Therefore, in practice, the side chain protecting groups commonly used with the Fmoc α-amino protection are not stable under the conditions used for Boc α-amino deprotection and the two types of α-amino protection schemes are not mixed in the assembly of a peptide chain by solid phase peptide synthesis. In addition, while the least expensive polymeric resin used in peptide synthesis, chloromethylated polystyrene or "Merrifield resin", is widely used with Boc protected amino acids, the literature suggests it is unsuitable for use with Fmoc protection on the α-amino group due to its lability in basic conditions. (see Stewart, et al., Solid Phase Peptide Synthesis (Pierce Chemical Co., 2d ed., 1984). The present invention is directed to a method for mixed usage of both Boc and Fmoc amino acids on "Merrifield resin" during solid phase synthesis of certain peptides.

Lanreotide® is an analog of somatostatin and is known to inhibit growth hormone release as well as inhibit insulin, glucagon and pancreatic exocrine secretion.

U.S. Pat. No. 4,853,371 discloses and claims Lanreotide®, a method for making it and a method for inhibiting the secretion of growth hormone, insulin, glucagon and pancreatic exocrine secretion.

U.S. Pat. No. 5,147,856 discloses the use of Lanreotide® of treating restenosis.

U.S. Pat. No. 5,411,943 discloses the use of Lanreotide® for treating hepatoma.

U.S. Pat. No. 5,073,541 discloses the use of Lanreotide® for treating lung cancer.

U.S. application Ser. No. 08/089,410 filed Jul. 9, 1993 discloses the use of Lanreotide® for treating melanoma.

U.S. Pat. No. 5,504,069 discloses the use of Lanreotide® for inhibiting the accelerated growth of a solid tumor.

U.S. application Ser. No. 08/854,941 filed May 13, 1997, discloses the use of Lanreotide® for decreasing body weight.

U.S. application Ser. No. 08/854,943 filed May 13, 1997, discloses the use of Lanreotide® for treating insulin resistance and Syndrome X.

U.S. Pat. No. 5,688,418 discloses the use of Lanreotide® for prolonging the survival of pancreatic cells.

PCT Application No. PCT/US97/14154 discloses the use of Lanreotide® for treating fibrosis.

U.S. application Ser. No. 08/855,311 filed May 13, 1997, discloses the use of Lanreotide® for treating hyperlipidemia.

U.S. application Ser. No. 08/440,061 filed May 12, 1995, discloses the use of Lanreotide® for treating hyperamylinemia.

U.S. application Ser. No. 08/852,221 filed May 7, 1997, discloses the use of Lanreotide® for treating hyperprolactinemia and prolactinomas.

The contents of the foregoing patents and patent applications are incorporated herein by reference.

DISCLOSURE OF INVENTION

This invention features a method for preparing a peptide comprising three or more amino acid residues having an N-terminal amino acid, a next to last amino acid adjacent to the N-terminal amino acid and a C-terminal amino acid, wherein said method comprises the steps of:

(a) attaching a first amino acid to a solid support resin through an ester bond to form a first-coupled-product, which comprises (i) reacting an aqueous solution of cesium carbonate with an alcohol solution of the first amino acid to form a cesium salt of the first amino acid, (ii) obtaining a solvent free cesium salt of the first amino acid, (iii) reacting the solid support resin with the cesium salt of the first amino acid in a dry polar aprotic solvent to form a first-coupled product;

wherein the first amino acid corresponds to the C-terminal amino acid of the peptide, the first amino acid's non-side chain amino group is blocked by a Boc and the first amino acid does not have a side chain functionality requiring protection, and the solid support resin is a chloromethylated polystyrene resin;

(b) deblocking the Boc from the first-coupled-product with an acid to form a first-deblocked-coupled-product;

(c) optionally coupling a next-amino-acid to the first-deblocked-coupled-product, which comprises reacting the next-amino-acid with the first-deblocked-coupled-product in an organic solvent comprising a peptide coupling reagent to form a next-blocked-coupled-product, wherein the next-amino-acid has a non-side chain amino group blocked by Boc and if the next-amino-acid has one or more side chain functionalities then the side chain functionalities do not require protection or the side chain functionalities have protecting groups that are stable to acid and base reagents used to deblock Boc and Fmoc, respectively;

(d) deblocking the Boc from the next-blocked-coupled-product which comprises reacting the next-blocked-coupled-product with a an acid to yield a next-deblocked-coupled-product;

(e) optionally repeating steps (c) and (d), each cycle forming an (X+1)-next-deblocked-coupled-product where X is the number of desired cycle repetitions;

(f) coupling a next-amino-acid to the first-deblocked-coupled-product from (b), or optionally to the (X+1)-next-deblocked-coupled-product from (e), which comprises reacting the next-amino-acid with said first-deblocked-coupled-product or said (X+1)-next-deblocked-coupled-product in an organic solvent comprising a peptide coupling reagent to form a next-blocked-coupled-product, wherein the next-amino-acid has a non-side chain amino group blocked by Fmoc, provided that if the next-amino-acid has one or more side chain functionalities then the side chain functionalities do not require protection or the side chain functionalities have protecting groups that are stable to base reagents used to deblock Fmoc;

(g) deblocking the Fmoc from the next-blocked-coupled-product which comprises reacting the next-blocked-coupled-product with a primary or secondary amine to yield a next-deblocked-coupled-product;

(h) optionally repeating steps (f) and (g), each cycle forming an (X+1)-next-deblocked-coupled-product where X is the desired number of cycle repetitions, until the next to last amino acid of the peptide is coupled and deblocked;

(i) coupling an N-terminal amino acid to the (X+1)-next-deblocked-coupled-product, which comprises reacting the N-terminal amino acid with the (X+1)-next-deblocked-coupled-product in an organic solvent comprising a peptide coupling reagent to form a completed-blocked-coupled-product, wherein the N-terminal-amino-acid has a non-side chain amino group blocked by Boc or Fmoc;

(j) deblocking the Boc or Fmoc group from the completed-blocked-coupled-product, which comprises reacting the completed-blocked-coupled-product with an acid in the case of Boc, or a base in the case Fmoc, to form a completed-peptide-resin-product;

(k) if side-chain functionalities are present on the completed-peptide-resin-product then optionally deprotecting the side-chain functionalities of the completed-peptide-resin-product, which comprises reacting the completed-peptide-resin-product with the appropriate deprotecting reagents to form a deprotected-completed-peptide-resin-product; and (l) cleaving the peptide from the solid support resin of the completed-peptide-resin-product or the deprotected-completed-peptide-resin-product to yield the peptide, which comprises reacting the completed-peptide-resin-product or the deprotected-completed-peptide-resin-product with ammonia, a primary amine or a secondary amine until the cleavage of the peptide from the resin is substantially complete;

provided that steps (f) and (g) must be carried out at least once in the synthesis of the peptide.

A preferred method of this invention is where the ammonia, primary amine or secondary amine of step (l) is in a solvent comprising an alcohol, and optionally, an aprotic polar solvent.

A preferred method of this invention is where step (l) further comprises the steps of:
precipitating the cleaved peptide from the solvent;
filtering the solid support resin and the precipitated peptide; and extracting the peptide in an acid solution to isolate the peptide.

A preferred method of this invention is where the first amino acid is Boc-L-Thr.

A preferred method of this invention is where the first amino acid is Boc-L-Thr-cesium salt yielding Boc-L-Thr-resin as the first-coupled-product and H-L-Thr-resin is the first-deblocked-coupled-product.

A preferred method of this invention is where the acid used to deblock the Boc group in step (j) is TFA.

A preferred method of the immediately foregoing method is where the organic solvent is methylene chloride, chloroform, or dimethylformamide and the peptide coupling reagent is diisopropylcarbodiimide, dicyclohexylcarbodiimide, or N-ethyl-N'-(3-dimethyl-aminopropyl) carbodiimide.

A preferred method of the immediately foregoing method comprises carrying out steps (f) and (g) six times after the formation of the first-deblocked-coupled-product of the formula H-L-Thr-resin wherein the following amino acids are coupled in the order of Fmoc-L-Cys(Acm), Fmoc-L-Val, Fmoc-L-Lys(Boc), Fmoc-D-Trp, Fmoc-L-Tyr(O-t-Bu) and Fmoc-L-Cys-(Acm) to form H-Cys(Acm)-Tyr(O-t-Bu)-D-Trp-Lys(Boc)-Val-Cys(Acm)-Thr-resin.

A preferred method of the immediately foregoing method comprises coupling Boc-D-β-Nal to H-Cys(Acm)-Tyr(O-t-Bu)-D-Trp-Lys(Boc)-Val-Cys(Acm)-Thr-resin according to step (c) to form Boc-D-β-Nal-Cys(Acm)-Tyr(O-t-Bu)-D-Trp-Lys(Boc)-Val-Cys(Acm)-Thr-resin.

A preferred method of the immediately foregoing method comprises simultaneously deblocking the Boc group blocking D-β-Nal, the O-t-Bu group protecting Tyr and the Boc group protecting Lys of Boc-D-β-Nal-Cys(Acm)-Tyr(O-t-Bu)-D-Trp-Lys(Boc)-Val-Cys(Acm)-Thr-resin according to step (j) to yield the completed-peptide-resin-product of the formula H-D-β-Nal-Cys(Acm)-Tyr-D-Trp-Lys-Val-Cys(Acm)-Thr-resin.

A preferred method of the immediately foregoing method comprises cleaving the peptide, H-D-O-Nal-Cys(Acm)-Tyr-D-Trp-Lys-Val-Cys(Acm)-Thr, from the solid resin by reacting H-D-β-Nal-Cys(Acm)-Tyr-D-Trp-Lys-Val-Cys(Acm)-Thr-resin with ammonia in a solvent comprising an alcohol, and optionally, an aprotic polar solvent until the cleavage is substantially complete to yield H-D-β-Nal-Cys(Acm)-Tyr-D-Trp-Lys-Val-Cys(Acm)-Thr-NH$_2$.

A preferred method of the immediately foregoing method is where the alcohol is methanol and the polar aprotic solvent is dimethylformamide.

A preferred method of the immediately foregoing method comprises simultaneously deprotecting the Acm groups protecting Cys and cyclizing the resulting deprotected Cys residues of the completed-peptide-product of the formula H-D-β-Nal-Cys(Acm)-Tyr-D-Trp-Lys-Val-Cys(Acm)-Thr-NH$_2$ by reacting H-D-β-Nal-Cys(Acm)-Tyr-D-Trp-Lys-Val-Cys(Acm)-Thr-NH$_2$ with a solution of iodine in an alcohol until the deprotecting and cyclizing is substantially complete to yield H-D-β-Nal-[Cys-Tyr-D-Trp-Lys-Val-Cys]-Thr-NH$_2$.

A preferred method of this invention is where the peptide is H-D-β-Nal-[Cys-Tyr-D-Trp-Lys-Val-Cys]-Thr-NH$_2$.

A preferred method of the immediately foregoing method is where the peptide is a somatostatin analog.

Definitions of terms used in the description of the present invention are as follows:

"first amino acid": encompasses any amino acid having its non-side chain amino group protected by Boc, which are commercially available or can be synthesized according to methods known to one of ordinary skill in the art, e.g., Boc-L-Thr;

"first-coupled-product": describes the product, which is attached to the solid support resin, resulting from the coupling of a first amino acid to the solid support resin, e.g. Boc-L-Thr-resin;

"first-deblocked-coupled-product": describes the product resulting from the removal or deblocking of the Boc group from the first-coupled-product, e.g., H-L-Thr-resin, where the "H" represents the available hydrogen of the non-side chain amino group resulting from the deblocking step;

"next-amino-acid": describes any amino acid having its non-side chain amino group protected by Boc or Fmoc, which are commercially available or can be synthesized according to methods known to one of ordinary skill in the art. Since step (c) and step (f) can be in a repeating cycle wherein the step is carried out more than once, each time step (c) or step (f) is carried out a next-amino-acid can be independently selected from the group of known and synthesizable amino acids having its non-side chain amino group protected by Boc or Fmoc, respectively;

"(X+1)-next-blocked-coupled-product": describes the product, which is attached to the solid support resin, resulting from the coupling of a next-amino-acid with the next-deblocked-coupled-product. Since steps (c) and (d) and steps (f) and (g) can be in a repeating cycle wherein additional next-amino-acids can be coupled, the term (X+1)-next-blocked-coupled-product is meant to represent the product resulting from each of the previous cycle of coupling;

"(X+1)-next-deblocked-coupled-product": describes the product resulting from the deblocking of the Fmoc group from the (X+1)-next-blocked-coupled-product;

"completed-peptide-resin-product": describes the peptide product, which is attached to the solid support resin, after the N-terminal amino acid has been attached to the peptide chain and after the N-terminal amino acid's non-side chain amino group has been removed or deblocked but which still has any of the side chain functionality protecting groups which were not removed by the reaction to deblock the N-terminal amino acid's non-side chain blocking group; and "deprotected-completed-peptide-resin-product": describes the peptide product, which is attached to the solid support resin, wherein any protecting groups of the amino acids' side chain functionalities have been removed or deprotected.

Examples of acids that can be used to deblock Boc are trifluoroacetic acid (TFA), methane sulfonic acid, and organic solutions containing HCl.

Examples of primary and secondary amines that can be used to deblock Fmoc are 4-(aminomethyl)piperidine, piperidine, diethylamine, DBU and tris(2-aminoethyl)amine.

Examples of non-nucleophilic bases that can be used for neutralizing the TFA salts of the freed amino group (RNH$_3^+$ CF$_3$COO$^-$, these salts must be converted to the "free" amine (NH$_2$) before or during coupling of the next amino acid or the coupling will not work) are diisopropylethylamine (DIEA) and triethylamine (TEA).

Examples of organic solvents that can be used for the amino acid coupling reactions are methylene chloride, chloroform, dichloroethane, dimethylformamide, dimethylacetamide, tetrahydrofuran, ethyl acetate, 1-methyl-2-pyrrolidinone, acetonitrile, or a combination of the above solvents.

Examples of peptide coupling agent include substituted carbodiimides such as diisopropylcarbodiimide, dicyclohexylcarbodiimide and N-ethyl-N'-(3-dimethyl-aminopropyl) carbodiimide.

The carboxyl and amino groups that participate in the formation of the peptide amide bond are called "non-side chain" carboxyl group or amino group, respectively. On the other hand, any functional groups of an amino acid which are not involved in formation of a peptide amide bond are called "side chain" functionalities.

The term "base-stable group" refers to protecting groups used to protect functionalities of the amino acids which (1) are base stable, e.g., cannot be removed by bases, such as 4-aminoethyl-piperidine, piperidine, or tris-(2-aminoethyl) amine, which are bases that are typically used to remove the protecting group Fmoc, and (2) can be removed by an acid, such as trifluoroacetic acid, or by other means, such as catalytic hydrogenation.

The symbol "Fmoc" and "Boc" are used herein and in the appended claims to mean 9-fluorenyl methoxycarbonyl and t-butyloxycarbonyl, respectively.

The above-described method can be used to prepare peptides, preferably somatostatin analogs, such as the octapeptide Lanreotide®, which has the following formula H-D-β-Nal-[Cys-Tyr-D-Trp-Lys-Val-Cys]-Thr-NH$_2$. When H-D-β-Nal-[Cys-Tyr-D-Trp-Lys-Val-Cys]-Thr-NH$_2$ is to be synthesized, the base-stable protecting groups used to block the side chain functionalities of Cys Lys, and Tyr can be acetamidomethyl (Acm), Boc, and t-butyl, respectively. Acm is preferred for Cys.

What is meant by a "somatostatin" analog is a peptide which exhibits biological activity similar (i.e., agonist) or opposite (i.e., antagonist) to that of somatostatin.

In the formula H-D-β-Nal-[Cys-Tyr-D-Trp-Lys-Val-Cys]-Thr-NH$_2$, each of the conventional three-letter amino acid symbols (e.g., Lys) represents a structural residue of an amino acid. For example, the symbol Lys in the above formula represents —NH—CH((CH$_2$)$_4$NH$_2$)—CO—. The symbol D-β-Nal represents the amino acid residue D-2-naphthylalaninyl. The brackets represent a disulfide bond attaching the free thiols of the two Cys residues of the peptide, indicating that the amino acids of the peptide within the brackets is cyclic.

One skilled in the art can, based on the description herein, utilize the present invention to its fullest extent.

Unless defined otherwise, all technical and scientific terms used herein have the same meaning as commonly understood by one of ordinary skill in the art to which this invention belongs. Also, all publications, patent applications, patents, and other references mentioned herein are incorporated by reference.

A peptide can be made according to a method of the present invention according to the following procedure.

A solution of 0.5 molar equivalents of cesium carbonate in water is slowly added to a solution of 1 molar equivalents of a Boc-AA$^1$ (Bachem Calif., Torrance, Calif.), wherein AA$^1$ corresponds to the C-terminal amino acid, dissolved in an alcohol, preferably methanol. The resulting mixture is stirred for about 1 hour at room temperature, and then all of the alcohol and water are removed under reduced pressure yielding a dry powder of the cesium salt of Boc-$AA^1$. Merrifield resin, 1.0 equivalent, (chloromethylated polystyrene; 200-400 mesh, chloride incorporation of 1.3 meq/gram, Advanced ChemTech, Louisville, Ky. or Polymer Laboratories, Church Stretton, England) is rinsed with a chlorinated solvent, preferably dichloromethane (DCM), an alcohol, preferably methanol, and a polar aprotic solvent, preferably dimethylformamide (DMF). The Boc-$AA^1$ cesium salt powder is dissolved in a dry polar aprotic solvent, preferably DMF, and the solution is combined with the above washed resin. The slurry is gently mixed at about 45°-65° C., preferably 50°-60° C., for about 48 to 106 hours, preferably 85 to 90 hours under an inert atmosphere such as nitrogen. The resin is filtered and rinsed well with a polar aprotic solvent, preferably DMF, water, and finally an alcohol, such as MeOH. The Boc-$AA^1$-resin is dried under reduced pressure.

The Boc-$AA^1$-resin is added to a glass reactor with a coarse sintered glass filter bottom. The resin is rinsed with a chlorinated solvent, such as DCM, deblocked with an organic acid, preferably 25% TFA/DCM, rinsed briefly with a chlorinated solvent, such as DCM, and an alcohol, such as MeOH, is neutralized with an organic base, preferably triethylamine in DCM, and rinsed again with DCM and a polar aprotic solvent, such as DMF, to yield the deblocked $AA^1$-resin.

The deblocked $AA^1$-resin is then optionally coupled with any desired number of amino acids. If a subsequent amino acid is Fmoc protected on the α-amino group (Fmoc-$AA^x$), then the side-chain group must either not require protection (such as Fmoc-Gly, Fmoc-Ala, Fmoc-Phe or Fmoc-Threonine) or the side chain must be protected by a group that is resistant to removal base. A molar excess of the Fmoc-$AA^x$ (where x is the sequence number of the amino acid in the peptide, counted from the C-terminal) is coupled with the deblocked $AA^1$-resin using a peptide coupling reagent such as diisopropylcarbodiimide (DIC) in a mixture of DCM/DMF for about 60 minutes. The coupled resin is rinsed with DMF, alcohol and DCM to yield Fmoc-$AA^x$-$AA^1$-resin. The coupling can be checked by Kaiser ninhydrin method. The Fmoc-$AA^x$-$AA^1$-resin is then rinsed once with DMF and then deblocked with a solution of a base in an organic solvent such as piperidine in DMF to yield $AA^x$-$AA^1$-resin. The $AA^x$-$AA^1$-resin is then rinsed with DMF and then several times with both an alcohol, such as MeOH, and DCM. The $AA^x$-$AA^1$-resin is rinsed once for about 3 minutes with DMF, three times, preferably for about 2 minutes each with isopropanol (IPA), and three times, preferably for about 2 minutes each with DCM. The resin is then ready for further coupling with either an Fmoc protected amino acid as described above, or a Boc amino acid as described below.

Similarly, if any subsequent amino acid which is to be coupled to the deprotected $AA^1$-resin is chosen with Boc protection on the α-amino group (Boc-$AA^x$), then the side-chain group also must either not require protection (such as Boc-Gly, Boc-Ala, Boc-Phe or Boc-Threonine) or the side chain must be protected by a group that is resistant to removal by both acid and base such as Boc-Cys(S-Acm). A Boc-$AA^x$, if selected, is coupled with the same reagents and solvents as the Fmoc amino acids described hereinabove and can be checked for coupling completion by the Kaiser ninhydrin method. The Boc-$AA^x$-$AA^1$-resin is then deblocked with a solution of an acid in an organic solvent such as TFA in DCM to yield $CF_3CO^-H^+AA^x$-$AA^1$-resin. This resin is then rinsed with chlorinated solvents, such as DCM, and alcohol, such as MeOH, several times and neutralized with a non-nucleophilic base, such as triethylamine, in DCM and then rinsed several times more with a chlorinated solvent, such as DCM, to yield $AA^x$-$AA^1$-resin. The resin is then ready for further coupling with either a Boc or an Fmoc protected amino acid as described above.

Depending on the desired peptide sequence and the type of α-amino blocked amino acid used, whether Fmoc protected or Boc protected, the appropriate combination of the foregoing coupling procedures are executed until an amino acid is required in the sequence with a side chain having a protecting group which can be removed by either the base used to deblock the Fmoc on the α-amino group or by the acid used to deblock the Boc on the α-amino group. Such a protected amino acid may be N-α-Boc-N'-ε-Fmoc-Lysine or N-α-Fmoc-N'-ε-Boc-Lysine. Once this occurs, all of the subsequent amino acids' α-amino blocking groups chosen must be compatible with the side group protection chosen for that position until the N-terminal amino acid. That is, the side chain protecting groups must be stable against the deblocking agent used to deblock the subsequent α-amino blocking group. For the N-terminal amino acid, either a Boc or an Fmoc can be used as the α-amino blocking group since the deblocking of the N-terminal amino acid can simultaneously deprotect certain of the protected side chains without an adverse affect on the synthesis strategy of the peptide because no further amino acids will be added.

The completed peptide chain, which is still attached to the resin, must then be deprotected and deblocked. To remove any base stable protecting groups and α-amino blocking group of the N-terminal amino acid, if applicable, the peptide-resin is treated with an acid in an organic solvent, such as TFA in DCM. To remove any acid stable protecting groups and α-amino blocking group of the N-terminal amino acid, if applicable, the peptide-resin is treated with an organic base, such as piperidine in DMF. Or the acid stable groups can be left on for removal in the subsequent cleavage of the peptide by ammonia or an amine base. The deprotected peptide-resin is then rinsed with a chlorinated solvent, such as DCM, and an alcohol, such as MeOH, and is dried to constant weight under reduced pressure.

The peptide is cleaved from the resin and the C-terminal converted to an amide by suspending the peptide-resin in 3:1 MeOH/DMF. The suspension is cooled to about <10° C. under nitrogen, and anhydrous ammonia gas is added below the solvent surface until the solution is saturated, while the temperature is maintained at below about 10° C. The slurry is gently mixed for about 24 hours while allowing the temperature to increase to about 20° C. The reaction is checked for completion by monitoring the disappearance of the methyl ester intermediate by HPLC under appropriate conditions depending on the peptide. The reaction is cooled, and more anhydrous ammonia is added, as needed, until the area of the methyl ester is less than 10% of the area of the desired product peak on the HPLC. The slurry is cooled to about less than 10° C., and mixing is continued overnight to allow the peptide to precipitate. The precipitate and resin are filtered and rinsed with cold MeOH. The precipitate and resin are dried under reduced pressure, and the product is extracted from the resin with aqueous acetic acid.

If a peptide contains protected Cys residues within its sequence, the thiol groups of the Cys can be deprotected and cyclized according to the following procedure. The peptide having Acm-protected Cys groups is dissolved in aqueous acetic acid under nitrogen atmosphere. The solution is stirred rapidly, and a solution of iodine in alcohol is added in one portion. The mixture is stirred and tested by HPLC for completion of deprotection and then quenched by titration with a 2% sodium thiosulfate solution to a colorless endpoint. The crude mixture is purified by preparative chromatography on C8 packing with a 0.1 ammonium acetate/acetonitrile gradient buffer, desalted on C8 packing with a 0.25N acetic acid/acetonitrile gradient, and lyophilized to give the desired peptide.

MODE FOR CARRYING OUT THE INVENTION

The following example is provided to illustrate a method of the present invention and is not to be construed as limiting the scope thereof.

Example 1

H$_2$-D-β-Nal-[Cys-Tyr-D-Trp-Lys-Val-Cys]-Thr-NH$_2$

A) Boc-L-Thr-Resin

A solution of 2.58 grams of cesium carbonate in 2.5 ml of water was slowly added to a solution of 3.48 grams of Boc-L-Threonine (Bachem Calif., Torrance, Calif.) dissolved in 7 ml of methanol. The resulting mixture was stirred for about 1 hour at room temperature, and then all methanol and water were removed under reduced pressure yielding a dry powder of cesium salt of Boc-L-Threonine. 10 grams of Merrifield resin (chloromethylated polystyrene; 200-400 mesh, chloride incorporation of 1.3 meq/gram, Advanced ChemTech, Louisville, Ky.) was rinsed with dichloromethane (DCM), methanol (MeOH), and dimethylformamide (DMF) (2×70 ml each). The Boc-L-Threonine cesium salt powder was dissolved in 60 ml of dry DMF, and the solution was combined with the above washed resin. The slurry was gently mixed at about 50°-60° C. for about 85 to 90 hours under nitrogen atmosphere. The resin was filtered and rinsed well with DMF, deionized water, and finally MeOH. The Boc-Threonine resin was dried under reduced pressure at about 40° C. (Threonine incorporation=0.85±0.15 meq/gram of dry resin).

B) H-D-β-Nal-Cys(Acm)-Tyr-D-Trp-Lys-Val-Cys(Acm)-Thr-Resin 2.0 grams of Boc-Threonine resin from step A was added to a 50 ml glass reactor with a coarse sintered glass filter bottom (batch scale=1.74 mmole). The resin was rinsed two times for about 5 minutes each with DCM (20 ml), deblocked with 25% TFA/DCM (30 ml) once for about 2 minutes and once for about 25 minutes, rinsed three times for about 2 minutes with DCM (20 ml), isopropanol (IPA) (20 ml), and DCM (20 ml), neutralized two times for about 5 minutes with 10% triethylamine/DCM (20 ml), rinsed three times for about 2 minutes with DCM, and rinsed once for about 5 minutes with DMF (20 ml).

The deblocked resin was coupled with 1.8 grams (4.35 mmole, 2.5 eq.) of Fmoc-L-Cysteine(Acm) (Bachem, Calif.) and 683 µl (4.35 mmole, 2.5 eq) diisopropylcarbodiimide (DIC) in 14 ml of 2:1 DCM/DMF for about 1 hour. The coupled resin was rinsed once for about 3 minutes with DMF (20 ml), three times for about 2 minutes with isopropanol (IPA), and three times for about 2 minutes with DCM (20 ml). The coupling was checked by Kaiser ninhydrin method.

The coupled resin was then rinsed once with DMF and then deblocked with a solution of piperidine in DMF. The deblocked coupled resin was then rinsed with DMF and several times with both MeOH and DCM. The coupled resin was rinsed once for about 3 minutes with DMF (20 ml), three times for about 2 minutes with isopropanol (IPA)(20 ml), and three times for about 2 minutes each with DCM (20 ml). The coupling was checked by Kaiser ninhydrin method.

Each of the following protected amino acids were coupled with the rinsed resin using DIC in DMF/DCM and deblocked in the following order as described above: Fmoc-L-Valine, Fmoc-L-Lysine(Boc), Fmoc-D-Tryptophan, Fmoc-L-Tyrosine(O-t-Bu), and Fmoc-L-Cysteine(Acm) (all from Bachem Calif.), Boc-D-2-Naphthylalanine (Synthetech, Albany, Oreg.).

The completed peptide chain was deblocked and deprotected twice with 75:20:5 DCM/TFA/anisole (30 ml) for about 2 minutes and about 25 minutes, rinsed three times for about 2 minutes each with DCM (20 ml), IPA (10 ml), and DCM (20 ml), neutralized two times for about 5 minutes with 10% triethylamine/DCM (20 ml), and rinsed three times for about 2 minutes with DCM (20 ml) and MeOH (20 ml). The resin was dried under reduced pressure. Dry weight=3.91 grams (103% of theory).

C) H-D-β-Nal-Cys-(Acm)-Tyr-D-Trp-Lys-Val-Cys(Acm)-Thr-NH$_2$ 2.93 grams of the peptide loaded resin from step B (1.3 mmoles eq.) was suspended in 50 ml of 3:1 MeOH/DMF. The suspension was cooled to about <10° C. under nitrogen, and anhydrous ammonia gas was bubbled until saturated while the temperature was maintained at below about 10° C. The slurry was gently mixed for about 24 hours while allowing the temperature to increase to about 20° C. The reaction was checked for completion by monitoring the disappearance of the methyl ester intermediate by HPLC (Rt. ~14 minutes for methyl ester vs. Rt. ~9.3 minutes for amide product on VYDAC®, 5µ, 100 Å, C18 with 26% CH$_3$CN/0.1% TFA Isocratic, 1 ml/min, 220 nm). The reaction was cooled, and more anhydrous ammonia was added until the area of the methyl ester was less than 10% the area of the product peak on the HPLC. The slurry was cooled to about less than 10° C., and mixing was continued overnight to allow the peptide to precipitate. The precipitate and resin were filtered and rinsed with 15 ml of cold MeOH. The precipitate and resin were dried under reduced pressure, and the product was extracted from the resin with 50% aqueous acetic acid (3×30 ml portions). HPLC analysis showed 870 mg (0.70 mmoles) of the title product present in the mixture (96% purity on Isocratic HPLC system).

D) H-D-β-Nal-[Cys-Tyr-D-Trp-Lys-Val-Cys]-Thr-NH$_2$ 500 mg (0.40 mmoles) of the peptide from step C was dissolved in 300 ml of 4% acetic acid and heated to about 55° C. under nitrogen atmosphere. The solution was stirred rapidly, and a 2% w/v solution of iodine in 7.7 ml of MeOH (0.60 mmoles) was added in one portion. The mixture was stirred for about 15 minutes and then quenched by titration with a 2% sodium thiosulfate solution to a colorless end-point (~2 ml). The mixture was cooled to room temperature and filtered. The crude mixture was purified by preparative chromatography on C8 packing (YMC, Inc., Wilmington, N.C.) with a 0.1 ammonium acetate/acetonitrile gradient buffer, desalted on YMC C8 packing with a 0.25N acetic acid/acetonitrile gradient, and lyophilized to give 350 mg of the desired peptide at 99% purity.

From the above description, one skilled in the art can easily ascertain the essential characteristics of the present invention, and without departing from the spirit and scope thereof, can make various changes and modifications of the invention to adapt it to various uses and conditions. Thus, other embodiments are also within the claims.

The invention claimed is:

1. A method for preparing a peptide of the formula H-D-β-Nal-[Cys-Tyr-D-Trp-Lys-Val-Cys]-Thr-NH$_2$ or H-D-β-Nal-Cys(Acm)-Tyr-D-Trp-Lys-Val-Cys(Acm)-Thr comprising the steps of:
  (a) attaching a Boc-L-Thr to a solid support resin through an ester bond to form a first-coupled-product, the attaching step comprising
    (i) reacting an aqueous solution of cesium carbonate with an alcohol solution of the first amino acid to form a cesium salt of the Boc-L-Thr,
    (ii) removing the alcohol and water from the cesium salt of the Boc-L-Thr,
    (iii) reacting the solid support resin with the cesium salt of the Boc-L-Thr in a dry polar aprotic solvent to form a first-coupled product;
      wherein the solid support resin is a chloromethylated polystyrene resin and the first-coupled-product is Boc-L-Thr-resin;
  (b) deblocking the Boc from the first-coupled-product with an acid to form a first-deblocked-coupled-product;
  (c) coupling a next-amino-acid to the first-deblocked-coupled-product from (b), which coupling step comprises reacting the next-amino-acid with said first-deblocked-coupled-product in an organic solvent comprising a peptide coupling reagent to form a next-blocked-coupled-product, wherein the next-amino-acid has a non-side chain amino group blocked by Fmoc, provided that if the next-amino-acid has one or more side chain functionalities then the side chain functionalities do not require protection or the side chain functionalities have protecting groups that are stable to base reagents used to deblock Fmoc;
  (d) deblocking the Fmoc from the next-blocked-coupled-product which deblocking step comprises reacting the next-blocked-coupled-product with a primary or secondary amine to yield a next-deblocked-coupled-product;
  (e) repeating steps (c) and (d) six times after the formation of the first-deblocked-coupled-product of the formula H-L-Thr-resin wherein the next amino acids Fmoc-L-Cys(Acm), Fmoc-L-Val, Fmoc-L-Lys(Boc), Fmoc-D-Trp, Fmoc-L-Tyr(O-t-Bu) and Fmoc-L-Cys-(Acm) are successively coupled to form H-Cys(Acm)-Tyr(O-t-Bu)-D-Trp-Lys(Boc)-Val-Cys(Acm)-Thr-resin;
  (f) coupling Boc-D-β-Nal with H-Cys(Acm)-Tyr(O-t-Bu)-D-Trp-Lys(Boc)-Val-Cys(Acm)-Thr-resin wherein the coupling step comprises reacting Boc-D-β-Nal with H-Cys(Acm)-Tyr(O-t-Bu)-D-Trp-Lys(Boc)-Val-Cys(Acm)-Thr-resin in an organic solvent comprising a peptide coupling reagent to form a completed-blocked-coupled-product;
  (g) deblocking the Boc group from the completed-blocked-coupled-product, which comprises reacting the completed-blocked-coupled-product with an acid to form a completed-peptide-resin-product;
  (h) optionally deprotecting the side-chain functionalities of the completed-peptide-resin-product, which comprises reacting the completed-peptide-resin-product with the appropriate deprotecting reagents to form a deprotected-completed-peptide-resin-product; and
  (i) cleaving the peptide of formula H-D-β-Nal-[Cys(Acm)-Tyr-D-Trp-Lys-Val-Cys(Acm)-Thr from the solid support resin of the completed-peptide-resin-product or cleaving the peptide of formula H-D-β-Nal-[Cys-Tyr-D-Trp-Lys-Val-Cys]-Thr-NH$_2$ from the solid support resin of the deprotected-completed-peptide-resin-product to yield the peptide,
    wherein the cleaving step comprises reacting the completed-peptide-resin-product or the deprotected-completed-peptide-resin-product with ammonia, a primary amine, or a secondary amine to cleave the peptide from the resin, and wherein the ammonia, primary amine, or secondary amine is in a solvent comprising an alcohol.

2. The method according to claim 1, wherein the ammonia, primary amine, or secondary amine of step (i) is in a solvent comprising an alcohol and an aprotic polar solvent.

3. The method according to claim 1, wherein the cleaving step
  (i) further comprises the steps of:
    (a) precipitating the cleaved peptide from the solvent;
    (b) filtering the solid support resin and the precipitated peptide; and
    (c) extracting the peptide in an acid solution to isolate the peptide.

4. The method according to claim 1, wherein the acid used to deblock the Boc group in step (g) is trifluoroacetic acid (TFA).

5. The method according to claim 1, wherein the organic solvent in step (c) is methylene chloride, chloroform, dimethylformamide, or mixture thereof and the peptide coupling reagent in step (c) is diisopropylcarbodiimide, dicyclohexylcarbodiimide, or N-ethyl-N'-(3-dimethyl-aminopropyl) carbodiimide.

6. The method according to claim 1, wherein the Boc group blocking D-β-Nal, the O-t-Bu group protecting Tyr and the Boc group protecting Lys of Boc-D-β-Nal-Cys(Acm)-Tyr(O-t-Bu)-D-Trp-Lys(Boc)-Val-Cys(Acm)-Thr-resin are simultaneously deblocked in step (j) to yield the completed-peptide-resin-product of the formula H-D-β-Nal-Cys(Acm)-Tyr-D-Trp-Lys-Val-Cys(Acm)-Thr-resin.

7. The method according to claim 6, which comprises cleaving the peptide, H-D-β-Nal-Cys(Acm)-Tyr-D-Trp-Lys-Val-Cys(Acm)-Thr, from the solid resin by reacting H-D-β-Nal-Cys(Acm)-Tyr-D-Trp-Lys-Val-Cys(Acm)-Thr-resin with ammonia in a solvent comprising an alcohol, and optionally, an aprotic polar solvent until the cleavage yields H-D-β-Nal-Cys(Acm)-Tyr-D-Trp-Lys-Val-Cys(Acm)-Thr-NH$_2$.

8. The method according to claim 7, wherein the alcohol is methanol and the polar aprotic solvent is dimethylformamide.

9. The method according to claim 8, further comprising simultaneously deprotecting the Acm groups protecting Cys and cyclizing the resulting deprotected Cys residues of the completed-peptide-resin-product of the formula H-D-β-Nal-Cys(Acm)-Tyr-D-Trp-Lys-Val-Cys(Acm)-Thr-NH$_2$ by reacting H-D-β-Nal-Cys(Acm)-Tyr-D-Trp-Lys-Val-Cys(Acm)-Thr-NH$_2$ with a solution of iodine in an alcohol until the deprotecting and cyclizing to yield H-D-β-Nal-[Cys-Tyr-D-Trp-Lys-Val-Cys]-Thr-NH$_2$.

10. The method of claim 1, wherein the cesium salt of the Boc-L-Thr obtained in step (a)(ii) is dry.

* * * * *